(12) United States Patent
Park et al.

(10) Patent No.: US 11,268,898 B2
(45) Date of Patent: Mar. 8, 2022

(54) TEMPERATURE AND HUMIDITY CHAMBER TYPE APPARATUS FOR TAKING POTENTIAL IMPACT MARKS AND METHOD USING THE SAME

(71) Applicant: REPUBLIC OF KOREA(NATIONAL FORENSIC SERVICE DIRECTOR MINISTRY OF PUBLIC ADMINISTRATION AND SECURITY), Wonju-si (KR)

(72) Inventors: Nam Kyu Park, Bucheon-si (KR); Jae Mo Goh, Wonju-si (KR); Jin Pyo Kim, Daejeon (KR); Young Il Seo, Wonju-si (KR); Eun Ah Joo, Yongin-si (KR); Je Hyun Lee, Wonju-si (KR); Sang Yoon Lee, Wonju-si (KR); Dong A Lim, Daejeon (KR); Kyung Mi Kim, Namyangju-si (KR)

(73) Assignee: REPUBLIC OF KOREA (MANAGEMENT: NATIONAL FORENSIC SERVICE DIRECTOR, MINISTRY OF PUBLIC ADMINISTRATION AND SECURITY), Wonju-si (KR)

( * ) Notice: Subject to any disclaimer, the term of this patent is extended or adjusted under 35 U.S.C. 154(b) by 225 days.

(21) Appl. No.: 16/574,832

(22) Filed: Sep. 18, 2019

(65) Prior Publication Data
US 2020/0363317 A1 Nov. 19, 2020

(30) Foreign Application Priority Data
May 17, 2019 (KR) ........................ 10-2019-0058095

(51) Int. Cl.
*G01N 21/01* (2006.01)
*G01N 21/77* (2006.01)
(Continued)

(52) U.S. Cl.
CPC ................ *G01N 21/01* (2013.01); *A61L 2/10* (2013.01); *B01L 1/025* (2013.01); *G01N 21/77* (2013.01);
(Continued)

(58) Field of Classification Search
CPC ...... G01N 21/01; G01N 21/77; G01N 33/367; G01N 33/68; G01N 2201/0231;
(Continued)

(56) References Cited

FOREIGN PATENT DOCUMENTS

| CN | 108853534 A | * | 11/2018 |
| KR | 10-2005-0105097 A | | 11/2005 |

(Continued)

OTHER PUBLICATIONS

Machine translation of CN 108853534. (Year: 2018).*
(Continued)

*Primary Examiner* — Jennifer Wecker
*Assistant Examiner* — Kathryn Elizabeth Limbaugh
(74) *Attorney, Agent, or Firm* — Hauptman Ham, LLP

(57) ABSTRACT

A temperature and humidity chamber type apparatus for taking potential impact marks according to an embodiment includes: a specimen treated with an amino acid reaction reagent to react with potential impact marks to take the potential impact marks; a chamber in which a receiving space for receiving the specimen is secured; a door for opening and closing the chamber; a supporter formed in the receiving space to receive the specimen; an adjuster for adjusting temperature and humidity in the chamber within a set application time range to take the potential impact marks; a display unit attached to one side of the outside of the chamber to display an operation state in the chamber; a power source; a controller for controlling setting of temperature, humidity, and an application time in the chamber;
(Continued)

and an input unit in which the controller operates according to a user's input.

13 Claims, 5 Drawing Sheets

(51) Int. Cl.
*A61L 2/10* (2006.01)
*G01N 33/36* (2006.01)
*B01L 1/02* (2006.01)
*G01N 33/68* (2006.01)

(52) U.S. Cl.
CPC ........... *G01N 33/367* (2013.01); *G01N 33/68* (2013.01); *B01L 2200/141* (2013.01); *B01L 2200/147* (2013.01); *B01L 2300/023* (2013.01); *B01L 2300/027* (2013.01); *B01L 2300/0609* (2013.01); *B01L 2300/10* (2013.01); *B01L 2300/168* (2013.01); *B01L 2300/18* (2013.01); *G01N 2201/0231* (2013.01); *G01N 2201/0238* (2013.01)

(58) Field of Classification Search
CPC ... G01N 2201/0238; A61L 2/10; B01L 1/025; B01L 2200/141; B01L 2200/147; B01L 2300/023; B01L 2300/027; B01L 2300/0609; B01L 2300/10; B01L 2300/168; B01L 2300/18
See application file for complete search history.

(56) References Cited

FOREIGN PATENT DOCUMENTS

| KR | 10-2009-0015563 A | 2/2009 |
| KR | 10-1913752 B1 | 10/2018 |
| KR | 10-1913752 | 11/2018 |

OTHER PUBLICATIONS

Machine translation of KR10-2005-0105097 (Year: 2005).*
Machine translation of KR10-2009-0015563 (Year: 2009).*
Korean Office Action for corresponding Korean application No. 10-2019-0058095 dated Apr. 13, 2021 with English Machine Translation.
Korean Office Action dated Sep. 1, 2020, in connection with corresponding Korean Patent Application No. 10-2019-0058095, citing the above references.

* cited by examiner ity, and an application time in a chamber by placing a specimen having a three-dimensional shape treated with an amino acid reaction reagent in the chamber to more precisely confirm whether the potential impact marks appear, and a method of taking potential impact marks using the temperature and humidity chamber type apparatus for taking potential impact marks.

2. Description of the Related Art

When an assault or other impact is applied to a victim at a crime scene, friction due to strong pressure creates potential impact marks that are caused by attaching sweat or keratin from the skin of the inside of the victim's garment. As such, the potential impact marks provide crucial information about an object used in the event of an impact on the victim, which is important evidence in criminal investigations.

The human body's sweat contains many organic materials, and various amino acids may be detected from sweat. When a physical assault is applied to a victim in a garment, water-soluble secretions in the sweat are rapidly absorbed on the garment surface, water is evaporated during the absorption process, and residual mixtures of amino acids remain in the garment. However, potential impact marks formed by the residual mixtures of amino acids in the garment are hard to discern immediately by the naked eye at a crime scene. After an impact on the body of the victim in the garment, heat is applied to the inside of the victim's garment using an amino acid reaction reagent, and potential impact marks appear. In general, after application of various kinds of amino acid reaction reagents to the inside of the victim's garment, through wet heat treatment using a heated iron, visual and optical method are used to verify the appearance of the shape of an object (shoe, pouch, bat, etc.) used for impact.

In the case of paper or planar evidence, it is ironed and heated to take potential impact marks. However, in the case of a garment, since the garment has a three-dimensional shape, it is necessary to take potential impact marks while maintaining the three-dimensional shape of the garment for more precise investigation.

[Prior art document] Korean Patent Publication No. 10-1913752 (registered on Oct. 25, 2018)

SUMMARY

One or more embodiments include a temperature and humidity chamber type apparatus for taking potential impact marks capable of receiving a specimen treated with an amino acid reaction reagent in a chamber and applying heat and humidity while maintaining a three-dimensional shape, thereby taking potential impact marks, and a method of taking potential impact marks using the temperature and humidity chamber type apparatus for taking potential impact marks.

Additional aspects will be set forth in part in the description which follows and, in part, will be apparent from the description, or may be learned by practice of the presented embodiments.

According to one or more embodiments, a temperature and humidity chamber type apparatus for taking potential impact marks includes: a specimen treated with an amino acid reaction reagent to react with potential impact marks to take the potential impact marks; a chamber in which a receiving space for receiving the specimen is secured; a door for opening and closing the chamber; a supporter formed in the receiving space to receive the specimen; an adjuster for adjusting temperature and humidity in the chamber within a set application time range to take the potential impact marks; a display unit attached to one side of the outside of the chamber to display an operation state in the chamber; a power source; a controller for controlling setting of temperature, humidity, and an application time in the chamber; and an input unit in which the controller operates according to a user's input.

In an embodiment, at least a portion of the door may be formed of a transparent material so as to see the degree of appearance of potential impact marks of the specimen from the outside.

In an embodiment, the supporter may be formed in a rod shape so that the specimen may be hooked on the supporter while maintaining the three-dimensional shape of the specimen using a hooking member.

In an embodiment, the temperature and humidity chamber type apparatus may further include a shelf-shaped container which is detachably mountable in the chamber.

In an embodiment, the adjuster may include: a temperature adjuster for adjusting temperature in the chamber within a set range by supplying warm air into the chamber; a humidity adjuster for supplying moisture to the inside of the chamber to adjust the humidity in the chamber within a set range; and a time adjuster for adjusting the time for which the amino acid reaction reagent is applied to the specimen under set temperature and humidity within a set range.

In an embodiment, the temperature adjuster may adjust the temperature in the chamber within the range of about 0° C. to about 120° C.

In an embodiment, the humidity adjuster may adjust relative humidity in the chamber within the range of about 20% to about 80%.

In an embodiment, the time adjuster may adjust an application time within the range of about 0 minutes to about 60 minutes.

In an embodiment, the controller may select a first timer mode and a second timer mode according to a user's input, wherein alarm sound is generated when the set application time elapses in first timer mode setting, and when the set application time elapses in second timer mode setting, power operation of the power source may be terminated after the alarm sound is generated.

In an embodiment, the temperature and humidity chamber type apparatus may further include a sterilizer for reducing biological risk of the specimen in the chamber.

In an embodiment, the temperature and humidity chamber type apparatus may further include an air purifier including an internal circulation filter for purifying air in the chamber and an external exhaust unit for discharging the air in the chamber to the outside.

According to one or more embodiments, a method of taking potential impact marks using a temperature and humidity chamber type apparatus for taking potential impact marks includes: applying temperature and humidity to receive a specimen treated with an amino acid reaction reagent in a receiving space in a chamber so as to maintain a three-dimensional shape and adjusting the temperature and humidity in the chamber within a set application time range so that potential impact marks appear, and visually or optically confirming the appeared potential impact marks.

In an embodiment, the applying of the temperature and humidity may be an operation of adjusting temperature in the chamber within the range of about 0° C. to about 120° C. within a set application time range of about 0 minutes to about 60 minutes, and adjusting relative humidity in the chamber within the range of about 20% to about 80%.

According to embodiments, potential impact marks may precisely appear by applying heat and moisture to the entire surface of an amino acid reaction reagent-treated specimen while maintaining the specimen in a three-dimensional shape. In addition, according to embodiments, since amino acid reaction reagents applied to the specimen are various and sensitive to temperature, humidity and an application time, the temperature, humidity and application time may be adjusted optimally.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
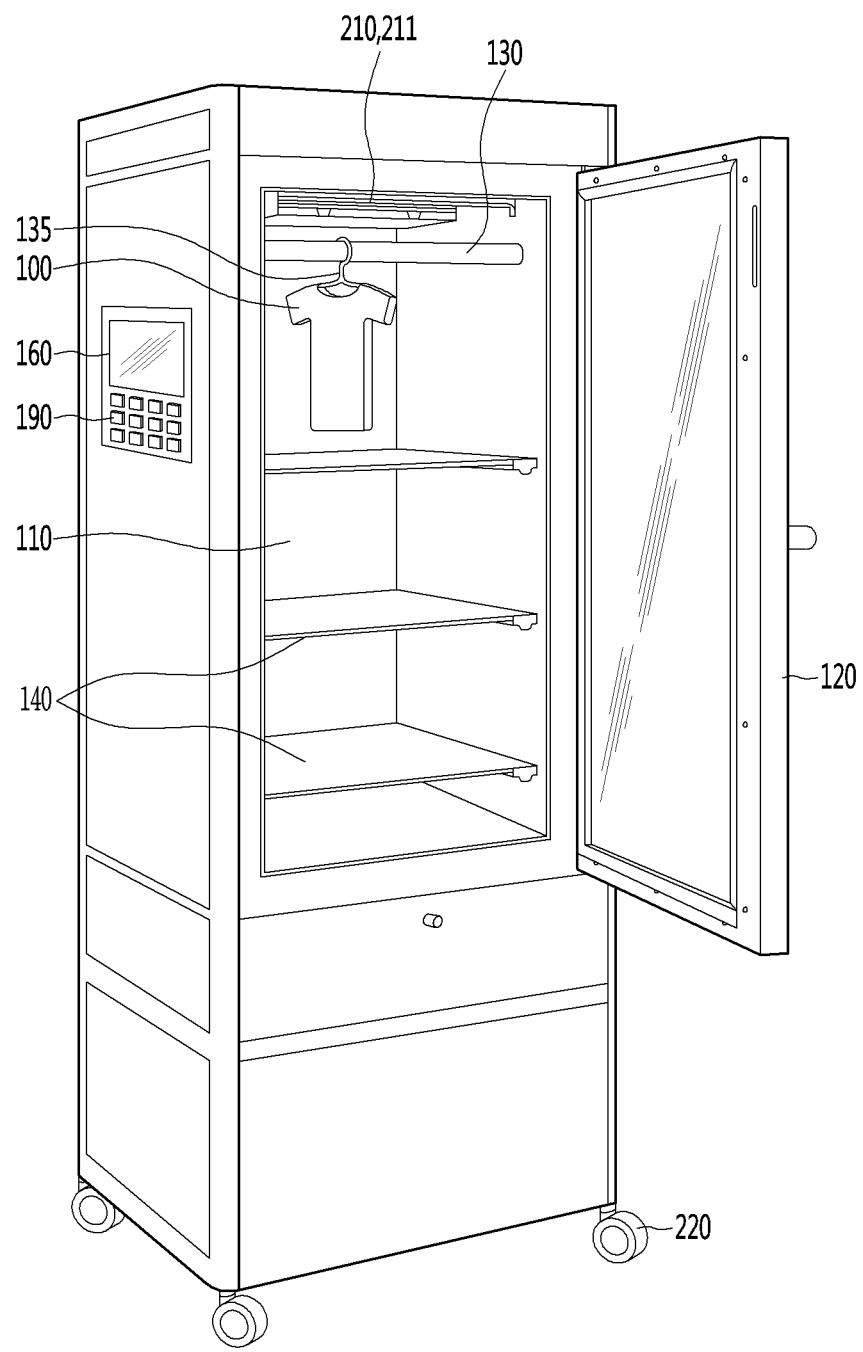
FIG. 1 is a schematic view of a temperature and humidity chamber type apparatus for taking potential impact marks according to an embodiment.

Reference will now be made in detail to embodiments, embodiments of which are illustrated in the accompanying drawings, wherein like reference numerals refer to like elements throughout.

It will be understood that although the terms "first", "second", etc. may be used herein to describe various components, these components should not be limited by these terms.

An expression used in the singular encompasses the expression of the plural, unless it has a clearly different meaning in the context.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly formed on the other layer, region, or component. That is, for example, intervening layers, regions, or components may be present.

Sizes of components in the drawings may be exaggerated for convenience of explanation. In other words, since sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

It will be understood that when a layer, region, or component is connected to another portion, the layer, region, or component may be directly connected to the portion or an intervening layer, region, or component may exist. For example, when a layer, region, or component is electrically connected to another portion, the layer, region, or component may be directly electrically connected to the portion or may be indirectly connected to the portion through another layer, region, or component.

Hereinafter, a temperature and humidity chamber type apparatus for taking potential impact marks according to an embodiment will be described with reference to FIGS. 1 to 3.

Figure 2:
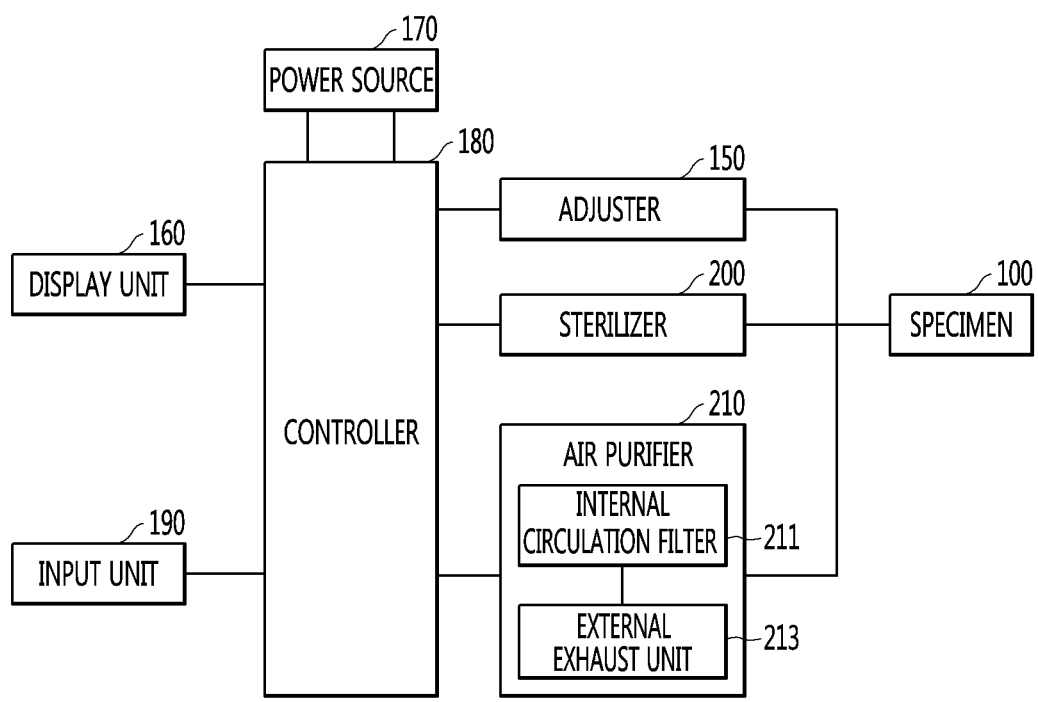
FIG. 2 is a block diagram of a temperature and humidity chamber type apparatus for taking potential impact marks according to an embodiment.
Figure 3:
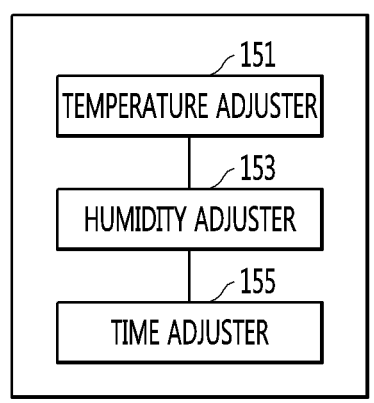
FIG. 3 is a block diagram of an adjuster of FIG. 2.

FIG. 1 is a schematic view of a temperature and humidity chamber type apparatus for taking potential impact marks according to an embodiment, FIG. 2 is a block diagram of the temperature and humidity chamber type apparatus for taking potential impact marks according to an embodiment, and FIG. 3 is a block diagram of an adjuster of FIG. 2.

Referring to FIGS. 1 to 3, the temperature and humidity chamber type apparatus for taking potential impact marks according to an embodiment may include a specimen 100, a chamber 110, a door 120, a supporter 130, an adjuster 150, a display unit 160, a power source 170, a controller 180, and an input unit 190, and may further include a container 140, a sterilizer 200, an air purifier 210, and a moving member 220.

The specimen 100 is an object to be tested, to which an amino acid reaction reagent capable of reacting with potential impact marks is applied. When a victim is assaulted directly or by an impacting device at a crime scene, secretions such as skin keratin and sweat are transferred to the victim's garment, leaving potential impact marks on the garment. The specimen 100 may be the garment or the like in which the potential impact marks of the victim may remain. Here, the specimen 100 is not necessarily limited to a garment, and anything may be possible as long as it is in contact with skin, and sweat, keratin, etc., which are secretions of the skin and transferred due to an impact such as assault, so that potential impact marks remain.

Since the specimen 100 is formed in a three-dimensional shape such as a garment in which potential impact marks remain, it is necessary to investigate the potential impact marks while keeping the three-dimensional shape. The victim's garment is the typical three-dimensional specimen 100, and anything that contacts the victim's skin or the like and to which secretions of the skin are transferred to take potential impact marks may be the specimen 100. In the case where potential impact marks of the specimen 100 as a garment appear through wet heat treatment using a heated iron, the specimen 100 may be heat-treated in a planar shape. Since wrinkles are generated in the process of heat-treating the specimen 100 in a planar form as described above, it is difficult to preserve the appeared potential impact marks and thus precise investigation may not be performed. Therefore, when heat and moisture are applied to the specimen 100 while the three-dimensional shape of the specimen 100 being maintained, potential impact marks may appear in a state where the potential impact marks are preserved. Thus, through the investigation of potential impact marks that are completely preserved and appeared on the specimen 100 in a three-dimensional shape, tools and methods that hit the victim may be determined more precisely.

The specimen 100 treated with the amino acid reaction reagent may react with potential impact marks on the specimen 100, thereby taking the potential impact marks. Ninhydrin, DFO, 1, 2-IND, zinc chloride, methanol, acetic acid, petroleum ether, ethyl acetate, and the like are examples of the amino acid reaction reagent to be applied to the specimen 100. In addition to the above, there are no restrictions on the types of amino acid reaction reagents that can be applied, as long as they react with potential impact marks to take the potential impact marks. The specimen 100 may take the potential impact marks through temperature and humidity control by applying heat and moisture in the chamber 110, which will be described later below.

The chamber 110 is a space in which a receiving space for receiving the specimen 100 is secured. The chamber 110 may have a receiving space having a certain volume so as to receive the three-dimensional shape of the specimen 100. The shape of the chamber 110 is not limited, and may be a rectangular parallelepiped as shown. The chamber 110 may be made of a material and a structure having durability so as to protect the safety of a user and minimize the risk in the process of receiving the specimen 100 and applying heat and moisture to the specimen 100.

The door 120 is for opening and closing the chamber 110. At least a portion of the door may be formed of a transparent material such as acrylic or tempered glass so as to be located on one side of the chamber 110 and to allow the inside of the chamber 110 to be viewed through. As shown, the door 120 may be connected to the chamber 110 by a hinge so as to be rotatable, but is not limited thereto. The door 120 is opened and the specimen 100 is received in the chamber 110 and then the door 120 is closed to change temperature and humidity in the chamber 110 for a certain time. Since at least a portion of the door 120 is formed of a transparent material, whether the potential impact marks of the specimen 100 treated with the amino acid reaction reagent appear and the degree of appearance of the potential impact marks in the process of changing the temperature and humidity in the chamber 110 may be directly visually confirmed by the user's eyes through the door 120.

Meanwhile, the temperature and humidity chamber type apparatus for taking potential impact marks may further include a locking device (not shown). When the temperature and humidity in the chamber 110 change, the door 120 may not be fixed, so that the door 120 may be fixed using a locking device.

The supporter 130 may be formed in the receiving space in the chamber 110 to receive the specimen 100. Referring to FIG. 1, the supporter 130 may be located in an upper portion of the chamber 110, and allows the specimen 100 to be mounted using a hooking member 135 to maintain the three-dimensional shape of the specimen 100. The supporter 130 may be formed into a rod shape as shown, and may mount a plurality of specimens 100 at the same time. The shape of the supporter 130 is not limited to the bar shape and any shape may be used as long as the specimen 100 can be mounted on the supporter 130 while the shape of the specimen 100 being maintained in three dimensions. For example, the cross section may be formed in a square shape instead of a circular shape like the rod shape. As such, the supporter 130 may mount the specimen 100 while maintaining the three-dimensional shape of the specimen 100, and allows a user to confirm whether the potential impact marks appear after the change of the temperature and the humidity in the chamber 110 in a state where the specimen 100 maintains the three-dimensional shape.

The container 140 is formed in a shelf shape detachably mountable in the chamber 110. Therefore, the container 140 may receive the specimen 100 even when the specimen 100 is not a garment but a shoe or the like. When the three-dimensional shape of the specimen 100 is maintained when the specimen 100 is received in the container 140 in a shelf shape, it is possible to confirm the potential impact marks while changing the temperature and humidity in the chamber 110 in a state where the specimen 100 is received in the container 140.

The adjuster 150 may adjust the temperature and humidity in the chamber 110 within a set application time range to take potential impact marks on the specimen 100. Referring to FIG. 3, the adjuster 150 may include a temperature adjuster 151, a humidity adjuster 153, and a time adjuster 155.

The temperature adjuster 151 may supply heat to the inside of the chamber 110 to adjust the temperature in the chamber 110 within a set range. The temperature in the chamber 110 for allowing the amino acid reaction reagent treated in the specimen 100 to take potential impact marks may include a temperature range of 0° C. to 120° C. The temperature adjuster 151 may include a heat supply capable of supplying heat into the chamber 110 and a temperature sensor.

The humidity adjuster 153 may supply moisture to the inside of the chamber 110 to adjust the humidity in the chamber 100 within a set range. The humidity in the chamber 110 for allowing the amino acid reaction reagent treated in the specimen 100 to take potential impact marks includes the range of 20% to 80% relative humidity. The humidity adjuster 153 may include a moisture generator capable of supplying moisture into the chamber 110, such as a humidifier, and a humidity sensor.

In addition, a circulation fan (not shown) may be installed at a certain position in the chamber 110 to uniformly maintain the temperature and humidity in the chamber 110. The heat and moisture supplied from the temperature adjuster 151 and the humidity adjuster 153 are introduced into the chamber 110 and the air in the chamber 110 is circulated through the circulation fan, so that the temperature and humidity in the chamber 110 may be maintained uniform and constant.

The time adjuster 155 may adjust time for applying the amino acid reaction reagent to the specimen 100 within a set range under set temperature and humidity in the chamber 110. Under the temperature and humidity set in accordance with the amino acid reaction reagent treated in the specimen 100, the application time necessary for allowing the potential impact marks to be appeared is in the range of about 0 minutes to about 60 minutes.

The temperature adjuster 151, the humidity adjuster 153, and the time adjuster 155 may be set differently depending on the kind of the amino acid reaction reagent treated in the specimen 100 as follows. The table below shows optimal conditions of the temperature, humidity, and application time set in the chamber 110 according to the kind of the amino acid reaction reagent treated in the specimen 100 for taking the potential impact marks.

| reagent | temperature | humidity | time |
|---|---|---|---|
| Ninhydrin | 27° C. | 65% | 5 to 10 minutes |
| DFO | 100° C. | 20% | 20 minutes |
| 1,2-IND | 100° C. | 65% | 20 minutes |

As described above, there is a difference in the extent to which the potential impact marks appear depending on the temperature, humidity, and application time in the chamber 110 depending on the kind of the amino acid reaction reagent. Accordingly, the adjuster 150 adjusts the temperature and humidity in the chamber 110 according to the kind of the amino acid reaction reagent applied to the specimen 100 so as to take the potential impact marks on the specimen 100.

The display unit 160 may be attached to one side of the outside of the chamber 110 to display an operation state in the chamber 110. The display unit 160 may display an on/off state of the power source 170, temperature and humidity in the chamber 110, a change in temperature in the chamber 110 during operation of the temperature adjuster 151, a change in humidity in the chamber 110 during operation of the humidity adjuster 153, an application time set through the time adjuster 155, whether a locking device is locked, and the like so that a user may recognize them.

The display unit 160 may include a liquid crystal display (LCD), a thin-film transistor LCD (TFT-LCD), a light emitting diode (LED), an organic LED (OLED), an active matrix OLED (AMOLED), a retina display, a flexible display, or a three-dimensional display.

The power source 170 may supply power to enable operation of the temperature and humidity chamber type apparatus for taking potential impact marks according to an embodiment. The power source 170 may supply power to the adjuster 150, the display unit 160, the controller 180, the input unit 190, and the like.

The controller 180 may perform the overall control operation of the temperature and humidity chamber type apparatus for taking potential impact marks according to an embodiment. The controller 180 may control the adjuster 150, the display unit 160, the power source 170, the input unit 190, the sterilizer 200, the air purifier 210, and the like.

The controller 180 controls an on/off state of the power source 170, and may supply power when the power source 170 is turned on. In addition, the controller 180 may control setting of the temperature, humidity, and application time in the chamber 110. The controller 180 may control the temperature adjuster 151 for adjusting the temperature in the chamber 110, the humidity adjuster 153 for adjusting the humidity in the chamber 110, and the time adjuster 155 for adjusting the application time of heat and moisture applied to the inside of the chamber 110, respectively.

The controller 180 may directly control setting of the temperature, humidity, and application time in the chamber 110 according to the temperature, humidity, and application time in the chamber 110 by the user's input. When a user inputs the type of amino acid reaction reagent to be treated in the specimen 100 to the input unit 190, the controller 180 may optimally control the setting of the temperature, humidity, and application time in the chamber 110 in which potential impact marks appear with respect to the amino acid reaction reagent. The controller 180 is programmed to set the temperature, humidity, and application time in the chamber 110 according to the type of the amino acid reaction reagent, and the setting of the temperature, humidity, and application time in the chamber 110 may be optimally controlled. For example, when a user selects 1, 2-IND as the amino acid reaction reagent to be applied to the specimen 100 through the input unit 190, the controller 180 sets the temperature in the chamber 110 to about 100° C., the humidity to about 65%, and the application time to about 20 minutes so that the potential impact marks on the specimen 100 may be controlled so as to be appeared under optimal conditions. The controller 180 may optimally control the setting of the temperature, humidity, and application time in the chamber 110 according to the appearance of the potential impact marks according to the selection of the kind of the amino acid reaction reagent.

Meanwhile, the controller 180 may select the first timer mode and the second timer mode according to a user's input. For example, the temperature in the chamber 110 is set to 27° C. and the humidity is set to 65% with respect to the specimen 100 to which Ninhydrin in the amino acid reaction reagent is applied, and the application time of heat and moisture may be set to about 10 minutes under the set temperature and humidity. Here, when the first timer mode is set by the user's input, an alarm sound such as a beep sound is generated when the set 10 minutes have elapsed. In addition, when the second timer mode is set by the user's input and the set 10 minutes have elapsed, power supply of the power source 170 is terminated after the alarm sound is generated.

The input unit 190 may transmit a selection signal input by a user, for example, a signal input in connection with setting and control of various functions, to the controller 180. In addition, the input unit 190 may include at least one of a keypad and a touchpad that generates an input signal according to a user's touch or operation. The input unit 190 may be configured in the form of a single touch panel (or a touch screen) together with the display unit 160 to simultaneously perform input and display functions.

A user may directly input the setting of the temperature, humidity, and application time in the chamber 110 in which the specimen 100 is received through the input unit 190. For example, the user may set the temperature in the chamber 110 to about 27° C. and the humidity to about 65% with respect to the specimen 100 treated with Ninhydrin in the amino acid reaction reagent, and may directly input the application time of heat and moisture for about 10 minutes under the set temperature and humidity. In this way, the temperature, humidity, and application time in the chamber 110 may be directly controlled according to the user's input. As described above, the user may select the type of the amino acid reaction reagent to be treated in the specimen 100 and input the selected reagent to the input unit 190. Thus, according to the input of the user's selection, the setting of the temperature, humidity, and application time in the chamber 110 may be optimally controlled.

The sterilizer 200 may sterilize the specimen 100 received in the chamber 110 to reduce biological risk that the specimen 100 at a crime scene may have on a user. For example, the sterilizer 200 may be a UV germicidal lamp, and the UV germicidal lamp may sterilize 99.9% of bacteria on the specimen 100 within 20 seconds. The input unit 190 may input whether the sterilizer 200 is operated, the controller 180 may control the operation of the sterilizer 200, and the display unit 160 may display whether the sterilizer 200 is operated.

The air purifier 210 purifies the air in the chamber 110 and discharges the air in the chamber 110 to the outside of the chamber 110. The air purifier 210 may include an internal circulation filter 211 and an external exhaust unit 213. The internal circulation filter 211 is for purifying air in the chamber 110, and the external exhaust unit 213 is for discharging the air in the chamber 110 to the outside. The external exhaust unit 213 is also called external exhaust. The air purifier 210 may be used when ventilation in the chamber 110 is required to use the chamber 110 again after potential impact marks appear by applying heat and moisture to the specimen 100 received in the chamber 110 for a set application time. The input unit 190 may input whether the air purifier 210 is operated, the controller 180 may control the operation of the air purifier 210, and the display unit 160 may display whether the air purifier 210 is operated.

The moving member 220 is formed at a lower end of the chamber 110 to allow a user to move the temperature and humidity chamber type apparatus for taking potential impact marks to a desired position. As shown in the drawings, the moving member 220 may be formed in the shape of a wheel at the lower end of the chamber 110, but is not limited thereto.

Meanwhile, the present disclosure may be used in the following modified embodiment.

Figure 4:
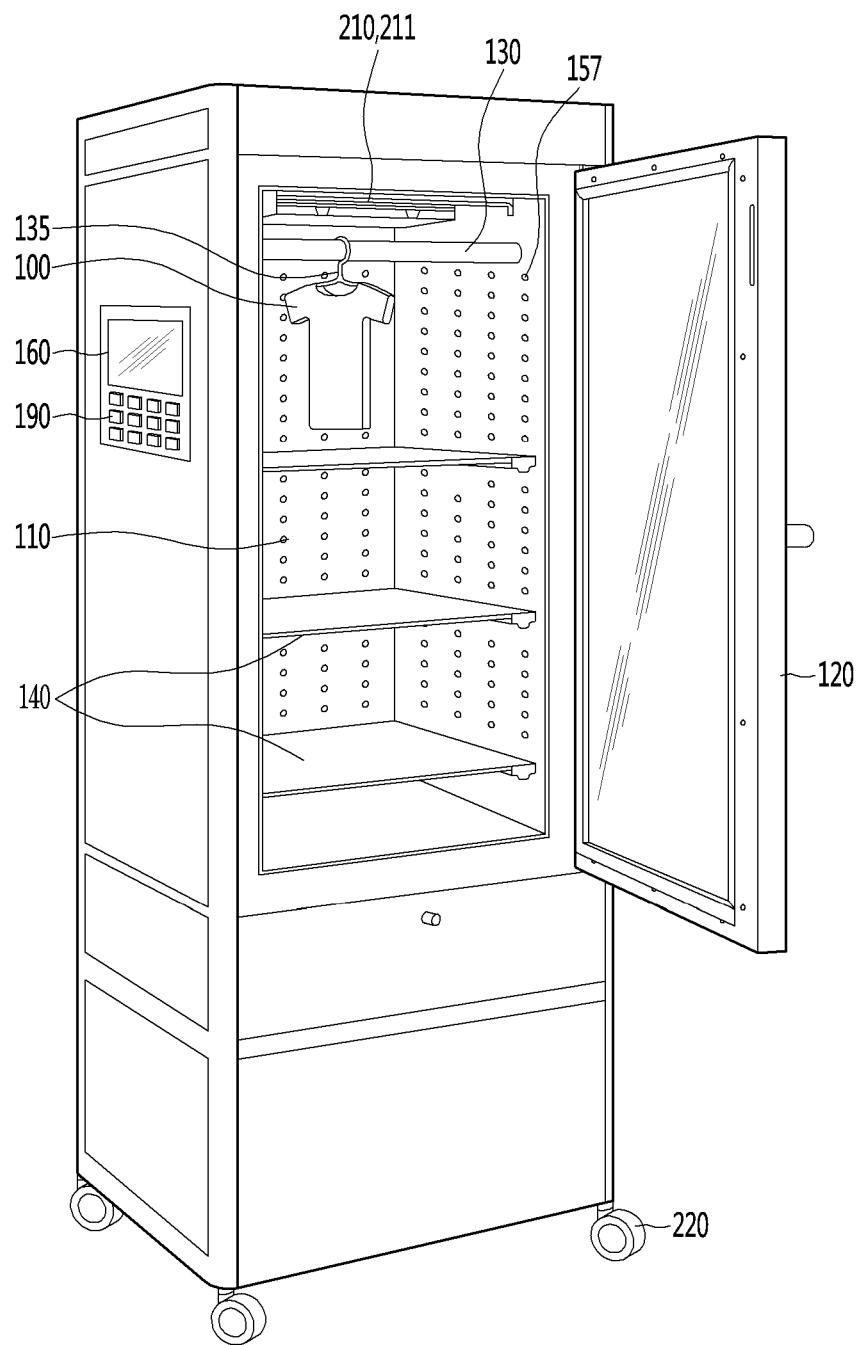
FIG. 4 is a view of a temperature and humidity chamber type apparatus for taking potential impact marks according to another embodiment.

FIG. 4 is a view of a temperature and humidity chamber type apparatus for taking potential impact marks according to another embodiment.

As shown in FIG. 4, the temperature and humidity chamber type apparatus for taking potential impact marks according to another embodiment may further include a temperature and humidity control groove 157. The temperature and humidity control groove 157 may simultaneously supply heat and moisture to adjust the temperature and humidity in the chamber 110. Temperature and humidity control grooves 157 may be formed in a hole shape and be spaced apart from each other on the surface of the inside of the chamber 110 at regular intervals. As such, heat and moisture may be uniformly supplied to the specimen 100 through the temperature and humidity control grooves 157, so that potential impact marks may appear.

Figure 5:
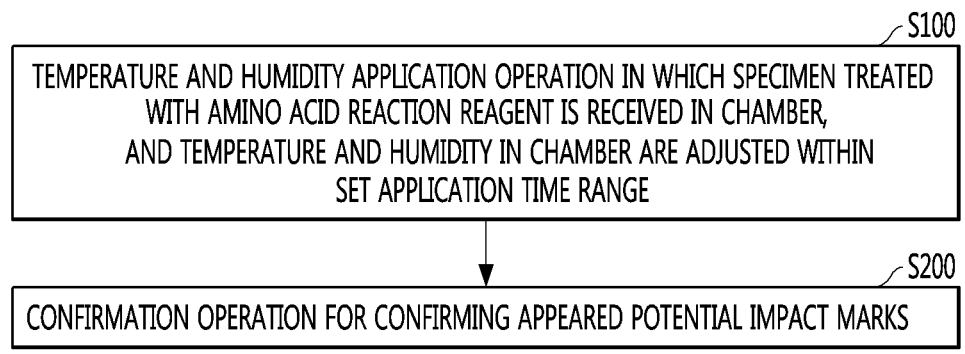
FIG. 5 is a flowchart illustrating a method of taking potential impact marks by using a temperature and humidity chamber type apparatus for taking potential impact marks according to an embodiment.

Hereinafter, a method of taking potential impact marks by using the temperature and humidity chamber type apparatus for taking potential impact marks according to an embodiment will be described with reference to FIG. 5. FIG. 5 is a flowchart illustrating the method of taking potential impact marks step by step by using the temperature and humidity chamber type apparatus for taking potential impact marks according to an embodiment.

Operation S100 is a temperature and humidity application operation in which the specimen 100 treated with an amino acid reaction reagent is received in a receiving space in the chamber 110 so as to maintain a three-dimensional shape, and temperature and humidity in the chamber are adjusted within a set application time range to apply heat and moisture to the specimen 100. Here, in order to take potential impact marks while maintaining the three-dimensional shape of the specimen 100 in the chamber 110, heat and moisture may be applied to the specimen 100 in a state in which the specimen 100 is hooked on the supporter 130 located in the chamber 110 using the hooking member 135. In operation S100 of the temperature and humidity application, within a set application time range of about 0 minutes to about 60 minutes, the temperature in the chamber 110 receiving the specimen 100 may be adjusted within the range of about 0° C. to about 120° C. and relative humidity in the chamber 110 may be adjusted within the range of about 20% to about 80%. The adjustment range of the temperature, humidity, and application time in the chamber 110 is the range of optimal temperature, humidity, and application time at which potential impact marks may appear on the specimen 100 treated with the amino acid reaction reagent. The temperature, humidity, and application time in the chamber 110 are different depending on the type of the amino acid reaction reagent.

Operation S200 is a confirmation operation for visually or optically confirming potential impact marks appeared in a state in which the specimen 100 maintains a three-dimensional shape. The potential impact marks appeared on the specimen 100 to which heat and moisture are applied for a certain period of time in the chamber 110 may be visually or optically confirmed. In the specimen 100 treated with the amino acid reaction reagent, characteristics according to the kind of the amino acid reaction reagent are utilized to confirm appeared potential impact marks by observing the appeared potential impact marks with the naked eye using a room lamp, or by photographing the appeared potential impact marks using optical characteristics.

It should be understood that embodiments described herein should be considered in a descriptive sense only and not for purposes of limitation. Descriptions of features or aspects within each embodiment should typically be considered as available for other similar features or aspects in other embodiments. Therefore, the scope of the present disclosure is defined by the appended claims.

As described above, a temperature and humidity chamber type apparatus for taking potential impact marks according to embodiments and a method of taking potential impact marks using the temperature and humidity chamber type apparatus for taking potential impact marks may take potential impact marks while maintaining the three-dimensional shape of a specimen such as a garment. Also, since heat and moisture are applied simultaneously to all sides of the specimen in the three-dimensional shape in which the amino acid reaction reagent is applied, it is possible to precisely analyze the potential impact marks while preserving the original state without wrinkling the specimen. According to the temperature and humidity chamber type apparatus for taking potential impact marks according to embodiments and the method of taking potential impact marks using the temperature and humidity chamber type apparatus for taking potential impact marks, since the amino acid reaction reagent applied to the specimen is sensitive to temperature, humidity, and an application time, the temperature, humidity, and application time may be precisely adjusted depending on the type of the amino acid reaction reagent applied to the specimen, so that the potential impact marks may appear in an optimized manner.

What is claimed is:

1. A temperature and humidity chamber type apparatus for taking potential impact marks, the temperature and humidity chamber type apparatus comprising:

a specimen treated with an amino acid reaction reagent to react with potential impact marks to take the potential impact marks;
a chamber in which a receiving space for receiving the specimen is secured;
a door configured to open and close the chamber;
a supporter formed in the receiving space to receive the specimen;
an adjuster configured to adjust temperature and humidity in the chamber within a set application time range to take the potential impact marks;
a display unit attached to one side of the outside of the chamber to display an operation state in the chamber;
a power source;
a controller configured to control setting of temperature, humidity, and an application time in the chamber;
an input unit in which the controller operates according to a user's input;
a sterilizer controlled by the controller, wherein the sterilizer is configured to sterilize the specimen received within the chamber, and reduce biological risk of the specimen in the chamber; and
a plurality of temperature and humidity control grooves on inner walls of the chamber, wherein the plurality of temperature and humidity control grooves is configured to simultaneously supply heat and moisture to adjust the temperature and humidity in the chamber.

2. The temperature and humidity chamber type apparatus of claim 1, wherein at least a portion of the door is formed of a transparent material so as to see the degree of appearance of potential impact marks of the specimen from the outside.

3. The temperature and humidity chamber type apparatus of claim 1, wherein the supporter is formed in a rod shape so that the specimen is hooked on the supporter while maintaining the three-dimensional shape of the specimen using a hooking member.

4. The temperature and humidity chamber type apparatus of claim 1, further comprising:
a shelf-shaped container which is detachably mountable in the chamber.

5. The temperature and humidity chamber type apparatus of claim 1, wherein the adjuster comprises:
a temperature adjuster configured to adjust temperature in the chamber within a set range by supplying warm air into the chamber;
a humidity adjuster configured to supply moisture to the inside of the chamber to adjust the humidity in the chamber within a set range; and
a time adjuster configured to adjust the application time for which the amino acid reaction reagent is applied to the specimen under set temperature and humidity within a set range.

6. The temperature and humidity chamber type apparatus of claim 5, wherein the temperature adjuster is configured to adjust the temperature in the chamber within the range of about 0° C. to about 120° C.

7. The temperature and humidity chamber type apparatus of claim 5, wherein the humidity adjuster is configured to adjust relative humidity in the chamber within the range of about 20% to about 80%.

8. The temperature and humidity chamber type apparatus of claim 5, wherein the time adjuster is configured to adjust the application time within the range of about 0 minutes to about 60 minutes.

9. The temperature and humidity chamber type apparatus of claim 1, wherein the controller is configured to select a first timer mode and a second timer mode according to a user's input, wherein an alarm sound is generated when the set application time elapses in first timer mode setting, and when the set application time elapses in second timer mode setting, power operation of the power source is terminated after the alarm sound is generated.

10. The temperature and humidity chamber type apparatus of claim 1, further comprising:
an air purifier comprising an internal circulation filter configured to purify air in the chamber and an external exhaust configured to discharge the air in the chamber to the outside.

11. A method of taking potential impact marks using a temperature and humidity chamber type apparatus for taking potential impact marks, the temperature and humidity chamber type apparatus including
a specimen treated with an amino acid reaction reagent to react with potential impact marks to take the potential impact marks;
a chamber in which a receiving space for receiving the specimen is secured;
a door configured to open and close the chamber;
a supporter formed in the receiving space to receive the specimen;
an adjuster;
a display unit attached to one side of the outside of the chamber to display an operation state in the chamber;
a power source;
a controller configured to control setting of temperature, humidity, and an application time in the chamber;
an input unit in which the controller operates according to a user's input;
a sterilizer controlled by the controller, wherein the sterilizer is configured to sterilize the specimen received within the chamber, and reduce biological risk of the specimen in the chamber; and
a plurality of temperature and humidity control grooves on inner walls of the chamber,
the method comprising:
applying temperature and humidity to receive the specimen treated with the amino acid reaction reagent in the receiving space in the chamber so as to maintain a three-dimensional shape and adjusting, by the adjuster, the temperature and humidity in the chamber within a set application time range so that potential impact marks appear; and
visually or optically confirming the appeared potential impact marks,
wherein the plurality of temperature and humidity control grooves simultaneously supplies heat and moisture to adjust the temperature and humidity in the chamber.

12. The method of claim 11, wherein the applying of the temperature and humidity comprises:
adjusting the temperature in the chamber within the range of about 0° C. to about 120° C. within a set application time range of about 0 minutes to about 60 minutes, and adjusting relative humidity in the chamber within the range of about 20% to about 80%.

13. The temperature and humidity chamber type apparatus of claim 1, wherein the plurality of temperature and humidity control grooves are spaced apart from each other at regular intervals.

* * * * *